United States Patent [19]
Clark, II

[11] Patent Number: 5,437,202
[45] Date of Patent: Aug. 1, 1995

[54] FLUID SAMPLING DEVICE

[75] Inventor: James E. Clark, II, Ojai, Calif.

[73] Assignee: Clark Technology Systems, Inc., Santa Paula, Calif.

[21] Appl. No.: 324,907

[22] Filed: Oct. 18, 1994

[51] Int. Cl.$^6$ ............................................. G01N 1/14
[52] U.S. Cl. .................................. 73/864.35; 222/394
[58] Field of Search ........... 73/863.71, 863.83, 864.34, 73/864.35; 222/21, 129, 205, 216, 251, 266, 335, 372, 373, 380, 394, 399, 425, 444

[56] References Cited

U.S. PATENT DOCUMENTS

| | | | |
|---|---|---|---|
| 3,798,972 | 3/1974 | Collins, Jr. ...................... | 73/863.71 |
| 3,986,401 | 10/1976 | Peterson ........................... | 73/864.35 |
| 4,271,704 | 6/1981 | Peters ................................ | 73/864.63 |
| 4,876,902 | 10/1989 | von Alfthan et al. ............ | 73/863.83 |

*Primary Examiner*—Robert Raevis
*Attorney, Agent, or Firm*—I. Morley Drucker; Howard N. Sommers; Daniel R. Kimbell

[57] ABSTRACT

A fluid sampling device for use in obtaining a precise volume of fluid to be sampled from a sealed vessel equipped with a hydraulic fitting to which the fluid sampling device is connectable. The device has a fluid sampling float chamber with an internally sealable top opening which opens into a bottom end of an air channel and a bottom opening which opens into a top end of a fluid channel. A floating ball is located in said fluid sampling float chamber and is sized to be sealingly sealable at the top opening. A vacuum generating means relying on air flow through a venturi to draw air out of the fluid sampling chamber through the air channel is located above the top opening of the float chamber. An air valve is located downstream of the venturi for controlling the direction of air flow though the venturi. A hydraulic coupler is located at a bottom end of the fluid channel which when connected to the hydraulic fitting on the sealed vessel opens, but when disconnected from the fitting closes. A drain line opens into the fluid channel above the hydraulic coupler, and is connected to a pressure relief valve.

19 Claims, 5 Drawing Sheets

FLUID SAMPLING DEVICE

BACKGROUND OF THE INVENTION

1. Field of the Invention

The invention relates to the art of collecting fluid samples, and more particularly to a fluid sampling device for obtaining precise volumes of fluid from a sealed container.

2. State of the Prior Art

The ability to take precise volumes of sample fluid from a fluid supply, at a precise depth in the fluid supply, is important in many industries including oil exploration, lubricant jobbing, and in the chemical and food industries, in order to identify the qualities of the fluid, to measure the presence of contaminants and to the detect the fluid's physical properties.

U.S. Pat. No. 4,271,704 to Peters discloses a fluid sampler for taking a sample of a fluid in an oil well. A chamber is pressurized with a floating ball so the floating ball seals off the top end of a chamber. The device is lowered into an oil well. When the hydrostatic pressure in the oil well exceeds the pressure in the chamber, oil will fill the chamber, float the floating ball to the top, and again seal off the chamber so that no more oil enters the device. U.S. Pat. No. 4,271,704 to Davidowicz et al. discloses a fluid sampling device with a chamber with two balls—one floating and one non-floating. By pressurizing and depressurizing the float chamber, a precise sample of fluid can be obtained. U.S. Pat. No. 4,715,789 to Liegel et al. discloses a valve assembly for controlling hydraulic fluids. It utilizes balls and springs, but not floating balls.

While these devices may be suitable for obtaining samples from unsealed containers, they are not specifically adapted for quick attachment and detachment to sealed pressure containers, to ensure that the contents of the sealed pressure container is not contaminated with outside air and/or dust. There accordingly remains a need for a device for obtaining fluid samples from a sealed container.

BRIEF DESCRIPTION OF THE INVENTION

The invention provides a fluid sampling device for use in obtaining a precise volume of fluid to be sampled from a sealed vessel with a fitting, to which the fluid sampling device is connectable, the fluid sampling device comprising:

- a fluid sampling float chamber with an internally sealable top opening, which top opening opens into a bottom end of an air channel, and a bottom opening which opens into a top end of a fluid channel;
- a floating ball located in said fluid sampling float chamber which is sized to be sealingly seatable on the top opening;
- a vacuum generating means relying on air flow through a venturi to draw air out of the fluid sampling chamber through the air channel which is located above the top opening of the float chamber;
- an air valve located downstream of said venturi for controlling the direction of air flow though the venturi;
- a coupler connected to a bottom end of the fluid channel, which when connected to the fitting on the sealed vessel opens, but when disconnected from the fitting closes;
- a drain line which opens into the fluid channel above said coupler, said drain line being connected to a pressure relief valve;
- wherein in the use of the fluid sampling device, the coupler of the device is coupled to the fitting on the sealed vessel, thereby opening a passageway from the sealed vessel to the fluid sampling float chamber, air flow is passed through the venturi and through the air valve to put a vacuum on the fluid sampling float to thereby cause fluid to flow therein from the sealed vessel until the floating ball floats into sealing contact with the top opening, the device is detached from the sealed vessel, thereby closing fluid flow through the coupler, and the air valve is closed to direct the air flow into the fluid sampling float chamber to expel the sampled volume of fluid out of the fluid sampling float chamber through the pressure relief valve and drain line.

The invention further provides a fluid sampling device for use in obtaining a precise volume of fluid to be sampled from a sealed vessel with a fitting, to which the fluid sampling device is connectable, the fluid sampling device comprising:

- a fluid sampling float chamber with top and bottom openings with a floating ball located therein, which ball can sealably seat at the top opening;
- a vacuum generating venturi having an air tube with an air entrance and an air exit, said air tube being in communication with the top opening of the float chamber;
- an air valve located downstream of the air exit;
- a coupler positioned below the bottom opening of the float chamber for connection to the sealed vessel, said coupler opening when coupled with the sealed vessel and closing when decoupled with the sealed vessel; and
- a pressure relief valve between the bottom opening and the coupler to vent fluid out of the fluid sampling float chamber, wherein in the use of the device, pressurized gas is passed through the air tube of the venturi to reduce the air pressure in the float chamber to draw fluid to be sampled therein, until the floating ball floats in the fluid into sealing contact with the top opening of the fluid chamber, after which the device is decoupled from the sealed vessel, closing the coupler, after which the air valve is closed, thereby directly air down into the float chamber, which propels the fluid out of fluid chamber through the pressure relief valve.

The invention yet further provides a fluid sampling device for use in obtaining a precise volume of fluid to be sampled from a sealed vessel, said fluid sampling device comprising:

- a fluid sampling float chamber with top and bottom opening with a floating ball locating therein, which ball is sealably seatable at the top opening;
- a venturi connected to the top opening of the fluid sampling float chamber;
- a pressure relief valve in fluid communication with the bottom opening of the fluid sampling float chamber; and an air valve downstream of the venturi to selectively direct air flow through one of (a) the venturi to draw air out of the fluid sampling float chamber to thereby cause the float chamber to draw up and fill with fluid to be sampled, until the floating ball seals off the top opening of the float chamber and (b) into float chamber to expel the fluid in the float chamber through the pressure relief valve.

DETAILED DESCRIPTION OF THE DRAWINGS

DETAILED DESCRIPTION OF THE INVENTION

Figure 1:
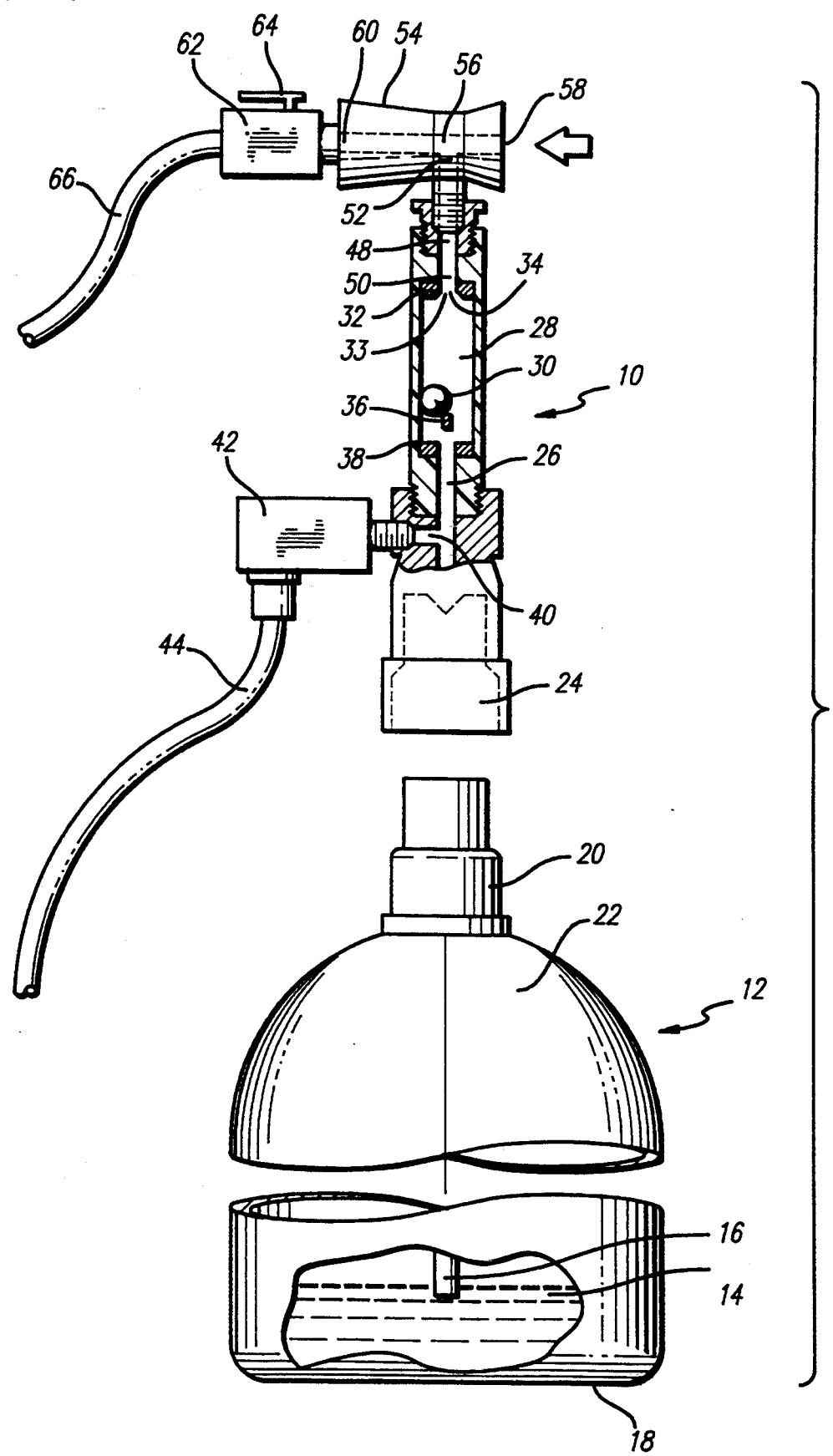
FIG. 1 is an exploded and partially exposed view depicting the fluid samples of the invention and the cylinder from which a sample is to be removed.

Referring to FIG. 1, the fluid sampler 10 and a cylinder 12 filled with a fluid 14 is shown. A suction tube 16 extends from near the bottom 18 of the cylinder 12 up to a fitting 20 at the top 22 of the cylinder 12. It is through this suction tube 16 that the sample of fluid 14 will be drawn up out of the cylinder 16. It is also through this suction tube 16 that the fluid 14 will be removed from the cylinder 14.

The fluid sampler device 10 has a coupler 24 which is engageable with the fitting 20. A main channel 26 connects the coupler 24 to a float chamber 28. The float chamber 28 has a floating ball 30 retained within. The free volume of the float chamber and its connected channels has a known volume, so that precise volumes of fluid to be sampled can be obtained.

The float chamber 28 has a sealing seat 32 with an opening 33 at its upper end 34 and a block means 36 at a lower end 38 of the float chamber 28 which prevents the floating ball 30 from sealing off the lower end 38 of the float chamber 28, yet which does not block fluid flow. The floating ball 30 can be conveniently formed of plastic material, or be a hollow aluminum ball, and is designed to float in the fluid being collected for sampling. Specifically, the weight of the floating ball 30 is made to be less than the weight of the volume of fluid displaced by the floating ball 30. The floating ball 30 is sized to freely move within the float chamber 28, yet fluidly tightly seat against the sealing seat 32. A side channel 40 connects to the main channel 26, and is connected to a pressure relief valve 42, which is designed to allow fluid out flow therefrom when pressure is delivered. A fluid drain line 44 connects to the pressure relief valve 42. The walls or a part (not shown) of the float chamber are preferably formed of transparent material so the user will know when the device is full of fluid to be sampled.

An air evacuation channel 48 communicates at its lower end 50 with the upper end 34 of the float chamber 28. An upper end 52 of the air evacuation channel 48 is in communication with a vacuum generating device, namely, a venturi 54 connected to a compressed air supply air supply (not shown). The venturi 54 has a venturi channel 56 with an air flow opening 58 and a downstream air flow exit 60. The upper end 52 of the air evacuation channel 48 connects to the venturi channel 56. A ballcock valve (or other valve) 62 with a handle 64 is located on the downstream air flow exit 60, and controls whether the airflow passes straight through the venturi channel 56 or down through the air evacuation channel 48 into the float chamber 28 and out through the pressure relief valve 42. A section of tubing or hose 66 is preferably connected to the ballcock valve 68, and is used to direct the air flow to a desired location, and which will carry any fluid which may inadvertently be expelled in the event that the floating ball 30 does not fluid tightly seat on the sealing seat 32.

The coupler 24 is of conventional design, which opens only when connected with the fitting 20 on the cylinder 12 but will close when decoupled from the fitting 20. The inventor has found that hydraulic type couplers and fitting function quite well, are readily available, are low in cost, and are reliable. Other types of quick connecting dry break type fittings which open when connected but close when disconnected can also be employed. Alternately, conventional one-way check valves which only allow fluid to flow into the float chamber, but not out, can be located downstream of the main channel 26, and used with any style of connector. (Not shown)

Figure 2:
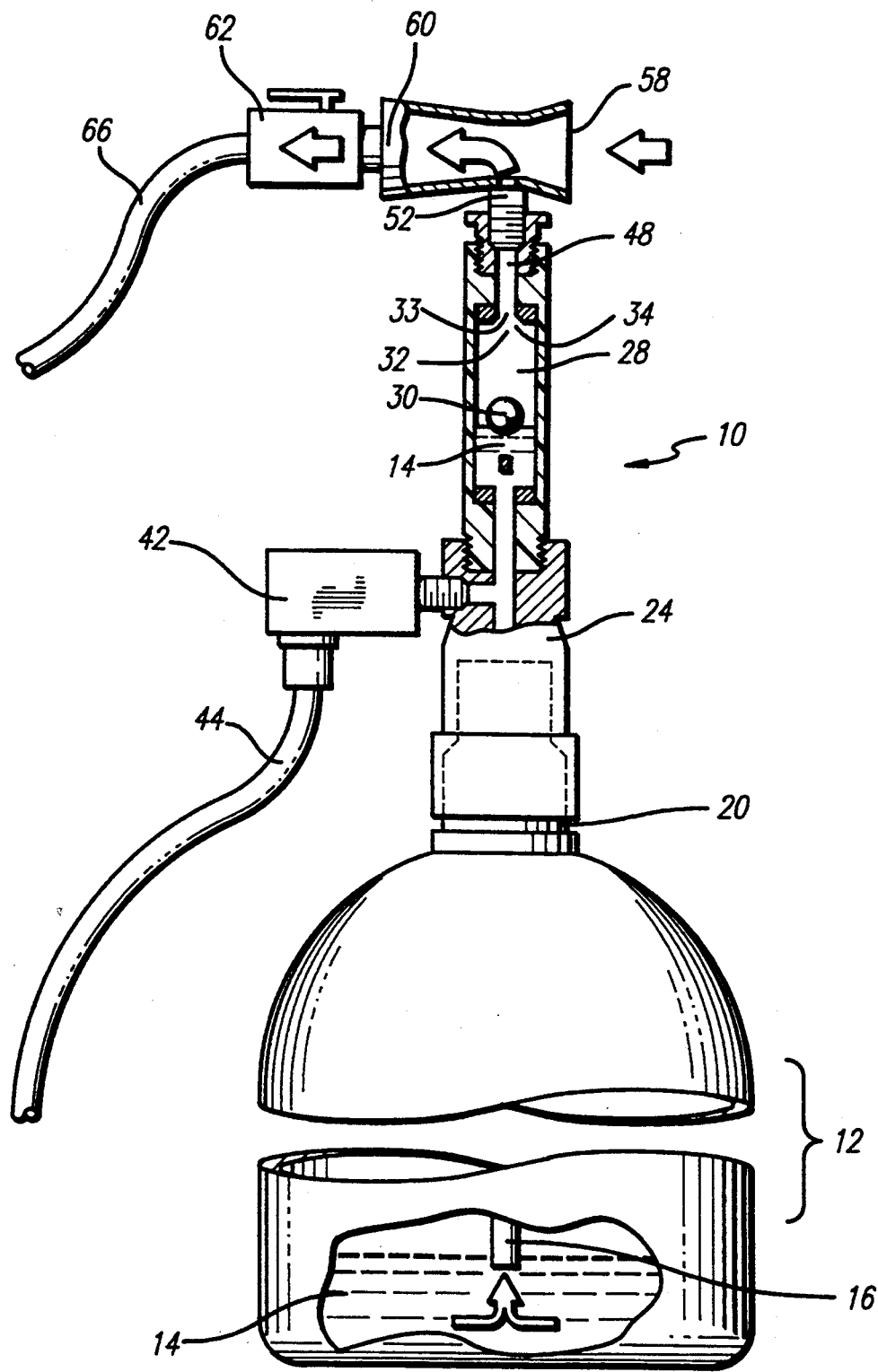
FIG. 2 is a side view of the fluid sampler connected to a cylinder with fluid to be sampled as the fluid is being collected.
Figure 3:
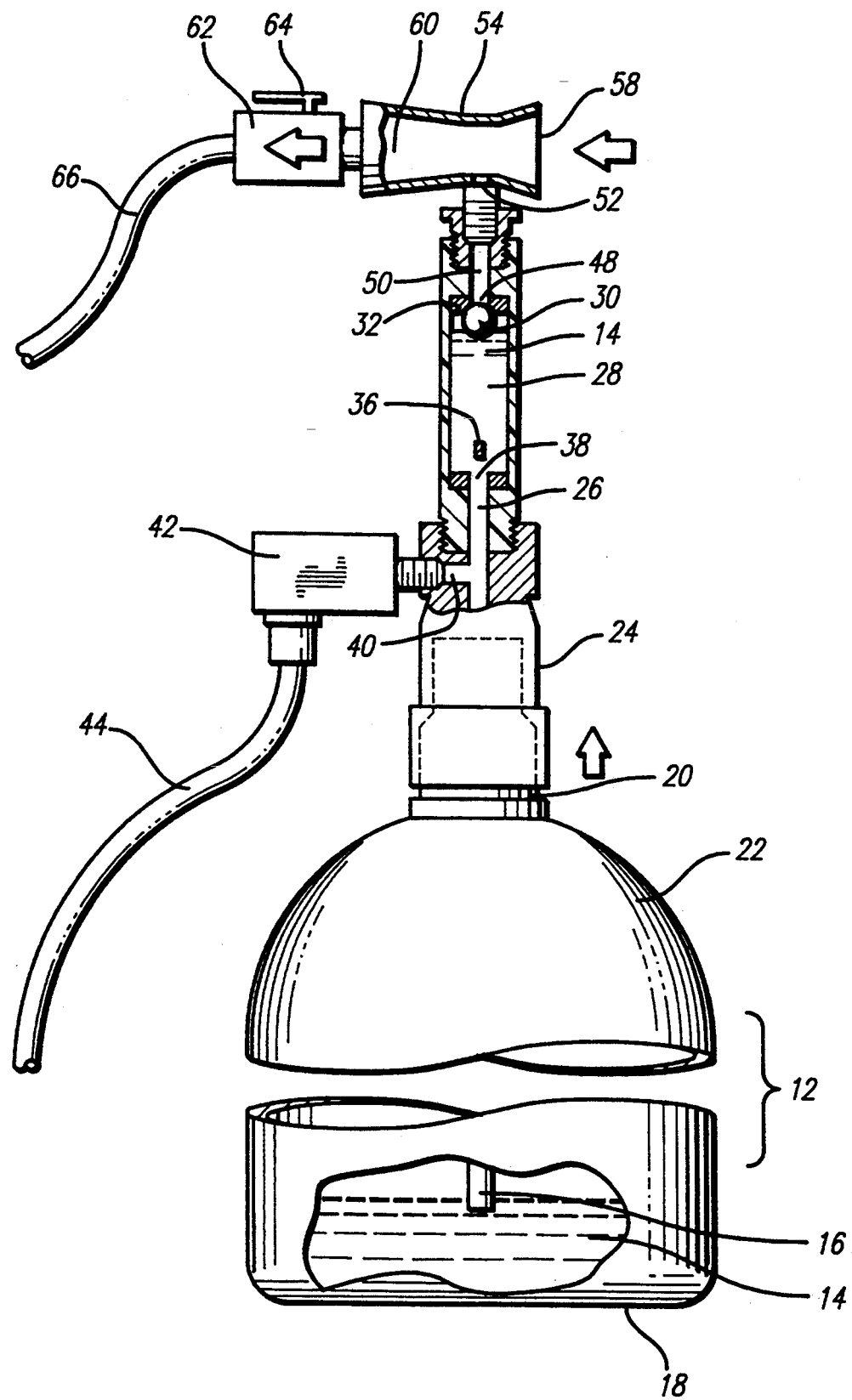
FIG. 3 is a side view of the fluid sampler filled with a precise volume of the sampled fluid.

Referring to FIGS. 2 and 3, the fluid sampler 10 is shown attached by a hydraulic coupler 24 to a hydraulic fitting 20 on the cylinder 12, with the ballcock valve 62 opened up. Pressurized air or other gas will thus flow through the venturi channel 56, and out the ballcock valve 62, which acts to draw air out of the float chamber 28, creating a low pressure zone therein. The fluid 14 in the cylinder 12 thus will be caused to flow up the suction tube 16 and into the float chamber 28. The rising level of fluid 14 in the float chamber 28 will cause the floating ball 30 to float up and seat on sealing seat 32 at the upper end 34 of the float chamber 28, thereby blocking off fluid flow through the opening 33. In this position, fluid 14 cannot be drawn out of the float chamber 28, and into the air evacuation channel 48 in communication with the venturi channel 56. FIG. 3 illustrates the float chamber 28 filled with a predetermined quantity of fluid 14 to be sampled.

Figure 4:
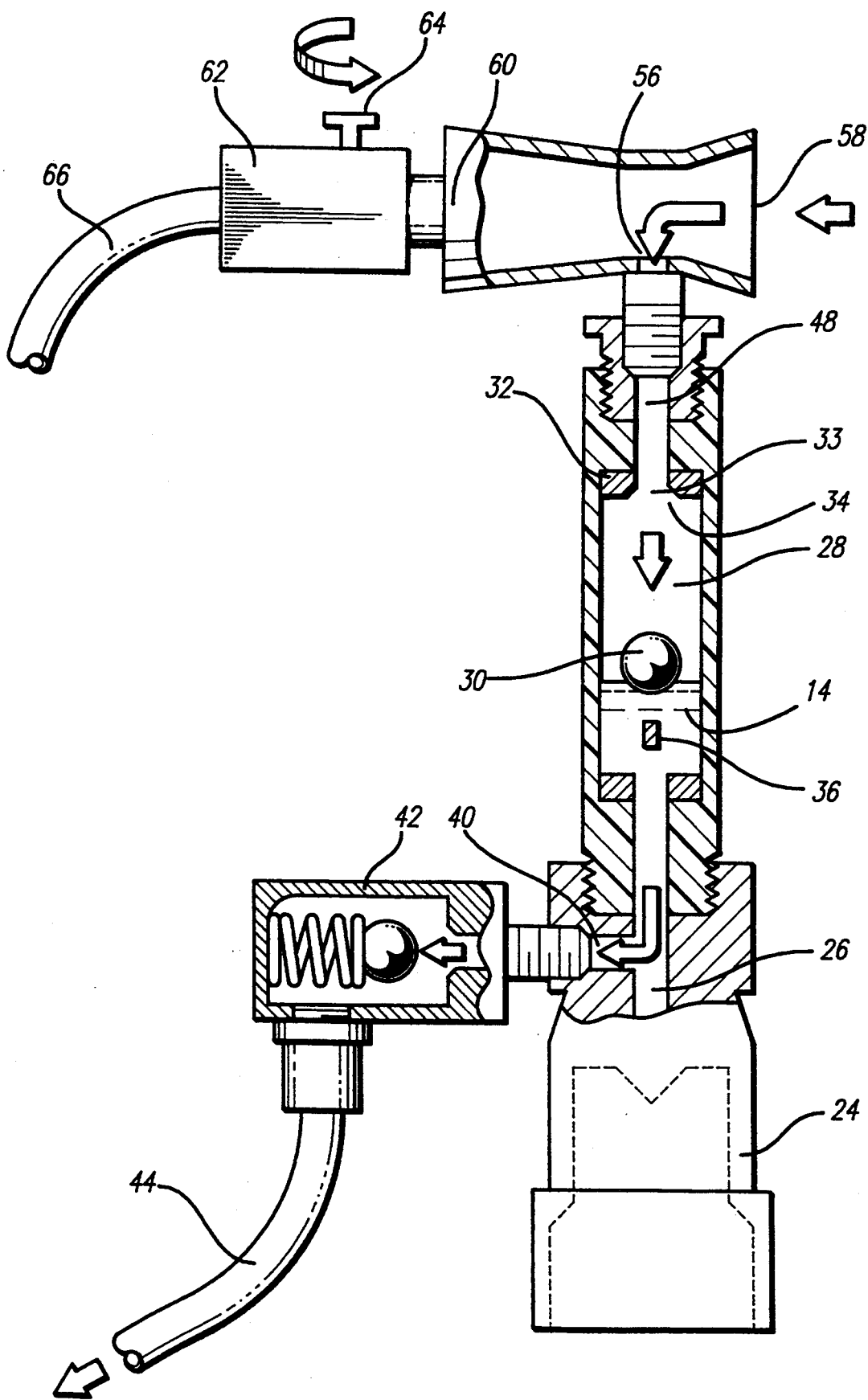
FIG. 4 is a side view of the fluid sampler with the fluid sample being expelled through the pressure relief valve.
Figure 5:
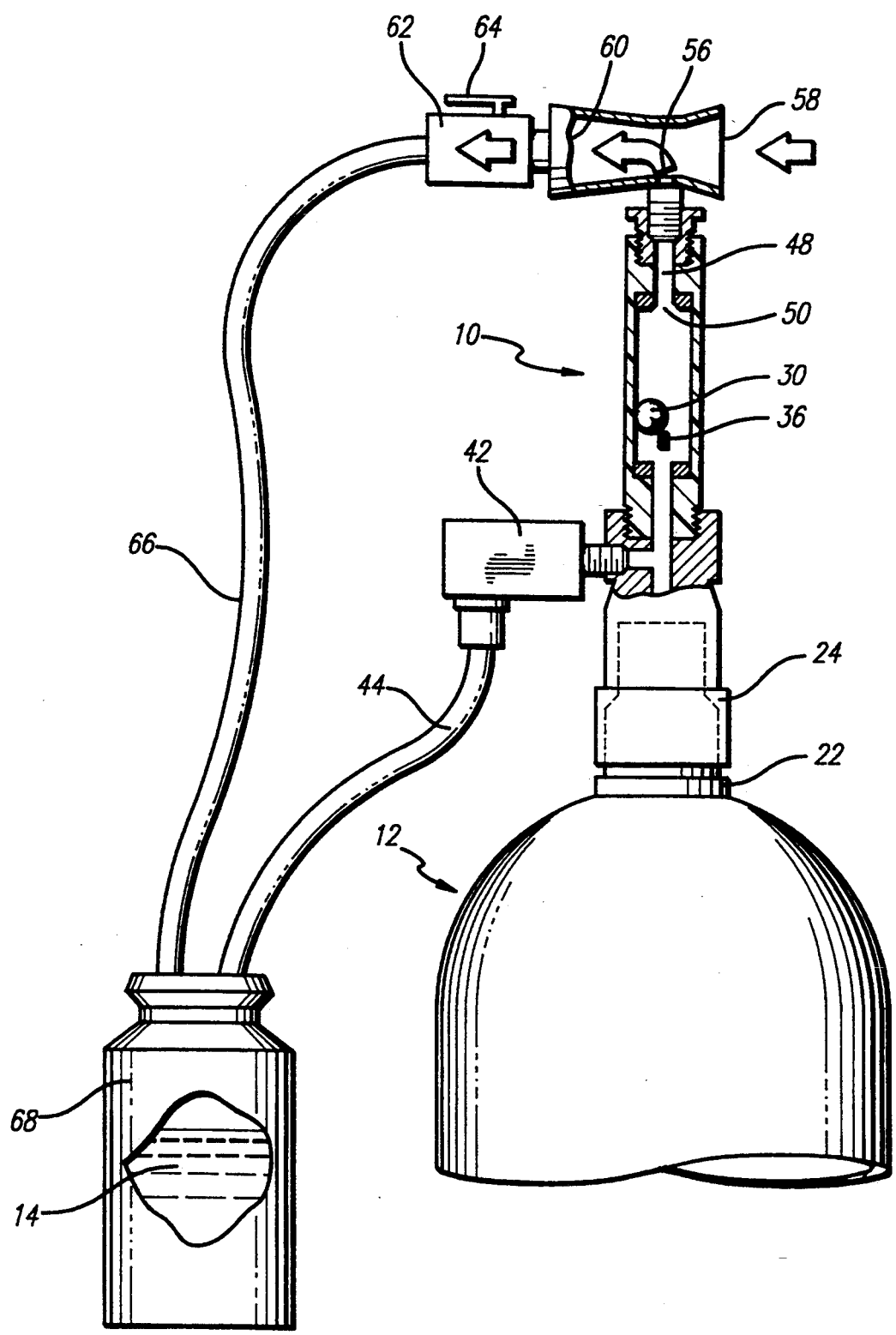
FIG. 5 is a side view of the fluid sampler after all the fluid sample has been expelled from the fluid sampler into a fluid sample collector container.

Turning to FIG. 4, with the ballcock valve 62 still opened (not shown), the fluid sampler device 10 is first removed from the cylinder 12 by disconnecting its hydraulic coupler 24 from the hydraulic fitting 20 on the cylinder 12. Doing so shuts off possible fluid flow out of the float chamber ball 28 through the hydraulic coupler 24. The ballcock handle 64 is then turned to shut off air flow through the ballcock valve 62. The pressurized air, no longer being able to travel through the ballcock valve 62, will then be forced down through the air evacuation channel 48 and into the float chamber 28. This exerts pressure on the sampled fluid 14 contained therein, pressurizing it, which activates the pressure relief valve 42, so the sample fluid will be expelled out of the float chamber 28 through the side channel 40, through the pressure relief valve 42, and out the fluid drain line 44, and into a fluid sampler container 68, as is best shown in FIGS. 4 and 5.

If the fluid sampler device is equipped with a one-way valve in lieu of or in conjunction with a hydraulic coupler 24, the fluid sampler device 10 need not be disconnected from the sealed cylinder 12 prior to expelling the sampled fluid from the float chamber 28 (not shown).

The collected fluid sample will thus be of a precise, predetermined volume, ideally suited for analysis and detection of contaminants.

The fluid collected device 10 thus provides an ideal device for collecting precise and predetermined volumes of sample fluids, in such a manner not to pollute the contents of the cylinder. For example, a single fluid sampling device 10 can be used to successively retrieve samples from a plurality of cylinders, into a common fluid collection container 68. An analysis can then be carried out the thusly commonly collected fluids. If the conglomeration of fluids passes muster, then no further testing of the individual cylinder is required. If the mixture of fluids does not meet the criterion, then further testing of the fluids from the individual or smaller groupings of cylinders can be conducted.

The drawings and the foregoing description are not intended to represent the only form of the invention in regard to the details of its construction and manner of operation. In fact, it will be evident to one skilled in the art that modifications and variations may be made without departing from the spirit and scope of the invention. Changes in form and in the proportion of parts, as well as the substitution of equivalents, are contemplated as circumstances may suggest or render expedient; and although specific terms have been employed, they are intended in a generic and descriptive sense only and not for the purpose of limitation, the scope of the invention being delineated in the following claims:

I claim:

1. A fluid sampling device for use in obtaining a precise volume of fluid to be sampled from a sealed vessel with a fitting, to which the fluid sampling device is connectable, the fluid sampling device comprising:
    a fluid sampling float chamber with an internally sealable top opening, which top opening opens into a bottom end of an air channel, and a bottom opening which opens into a top end of a fluid channel;
    a floating ball located in said fluid sampling float chamber which is sized to be sealingly seatable on the top opening;
    a vacuum generating means relying on air flow through a venturi to draw air out of the fluid sampling chamber through the air channel which is located above the top opening of the float chamber;
    an air valve located downstream of said venturi for controlling the direction of air flow though the venturi;
    a coupler connected to a bottom end of the fluid channel, which when connected to the fitting on the sealed vessel opens, but when disconnected from the fitting closes;
    a drain line which opens into the fluid channel above said coupler, said drain line being connected to a pressure relief valve;
    wherein in the use of the fluid sampling device, the coupler of the device is coupled to the fitting on the sealed vessel, thereby opening a passageway from the sealed vessel to the fluid sampling float chamber, air flow is passed through the venturi and through the air valve to put a vacuum on the fluid sampling float to thereby cause fluid to flow therein from the sealed vessel until the floating ball floats into sealing contact with the top opening, the device is detached from the sealed vessel, thereby closing fluid flow through the coupler, and the air valve is closed to direct the air flow into the fluid sampling float chamber to expel the sampled volume of fluid out of the fluid sampling float chamber through the pressure relief valve and drain line.

2. The fluid sampling device of claim 1, wherein at least a portion of the fluid sampling chamber has a see-through wall to allow for visual inspection of the interior of the float chamber.

3. The fluid sampling device of claim 1, wherein said device further comprises a drain tube downstream of the pressure relief valve to direct the sampled fluid out of the device.

4. The fluid sampling device of claim 1, wherein the pressure relief valve is triggered to open at a pressure less than that of the air pressure directed through the fluid sampling float chamber when the air valve is closed.

5. The fluid sampling device of claim 1, wherein the floating ball is a hollow aluminum ball.

6. The fluid sampling device of claim 1, wherein the fluid sampling device further comprises a fluid sample collection container for collecting the sampled fluid from the fluid sampling float chamber.

7. The fluid sampling device of claim 1, wherein the fitting on the sealed vessel and the coupler on the fluid sampling device are of a dry break type.

8. A fluid sampling device for use in obtaining a precise volume of fluid to be sampled from a sealed vessel with a fitting, to which the fluid sampling device is connectable, the fluid sampling device comprising:
    a fluid sampling float chamber with top and bottom openings with a floating ball located therein, which ball can sealably seat at the top opening;
    a vacuum generating venturi having an air tube with an air entrance and an air exit, said air tube being in communication with the top opening of the float chamber;
    an air valve located downstream of the air exit;
    a coupler positioned below the bottom opening of the float chamber for connection t,o the sealed vessel, said coupler opening when coupled with the sealed vessel and closing when decoupled from the sealed vessel; and
    a pressure relief valve between the bottom opening and the coupler to vent fluid out of the fluid sampling float chamber, wherein in the use of the device, pressurized gas is passed through the air tube of the venturi to reduce the air pressure in the float chamber to draw fluid to be sampled therein, until the floating ball floats in the fluid into sealing contact with the top opening of the fluid chamber, after which the device is decoupled from the sealed vessel, closing the coupler, after which the air valve is closed, thereby directly air down into the float chamber, which propels the fluid out of fluid chamber through the pressure relief valve.

9. The fluid sampling device of claim 8, wherein at least a portion of the fluid sampling chamber has a see-through wall to allow for visual inspection of the interior of the float chamber.

10. The fluid sampling device of claim 8, wherein said device further comprises a drain tube downstream of the pressure relief valve to direct the sampled fluid out of the device.

11. The fluid sampling device of claim 8, wherein the pressure relief valve is triggered to open at a pressure less than that of the air pressure directed through the fluid sampling float chamber when the air valve is closed.

12. The fluid sampling device of claim 8, wherein the floating ball is a hollow aluminum ball.

13. The fluid sampling device of claim 8, wherein the fluid sampling device further comprises a fluid sample collection container for collecting the sampled fluid from the fluid sampling float chamber.

14. The fluid sampling device of claim 8, wherein the fitting on the sealed vessel and the coupler on the fluid sampling device are of a dry break type.

15. A fluid sampling device for use in obtaining a precise volume of fluid to be sampled from a sealed vessel, said fluid sampling device comprising:
- a fluid sampling float chamber with top and bottom opening with a floating ball locating therein, which ball is sealably seatable at the top opening;
- a venturi connected to the top opening of the fluid sampling float chamber;
- a pressure relief valve in fluid connection with the bottom opening of the fluid sampling float chamber; and
- an air valve downstream of the venturi to selectively direct air flow through one of (a) the venturi to draw air out of the fluid sampling float chamber to thereby cause the float chamber to draw up and fill with fluid to be sampled, until the floating ball seals off the top opening of the float chamber and (b) into float chamber to expel the fluid in the float chamber through the pressure relief valve.

16. The fluid sampling device of claim 15, wherein at least a portion of the fluid sampling chamber has a see-through wall to allow for visual inspection of the interior of the float chamber.

17. The fluid sampling device of claim 8, therein said device further comprises a drain tube downstream of the pressure relief valve to direct the sampled fluid out of the device.

18. The fluid sampling device of claim 8, wherein the pressure relief valve is triggered to open at a pressure less than that of the air pressure directed through the fluid sampling float chamber when the air valve is closed.

19. The fluid sampling device of claim 15, wherein the fitting on the sealed vessel and the coupler on the fluid sampling device are of a dry break type.

* * * * *